United States Patent
Dwarika et al.

(10) Patent No.: US 12,332,085 B2
(45) Date of Patent: *Jun. 17, 2025

(54) WEARABLE APPARATUS

(71) Applicant: HEALTH CARE ORIGINALS, INC., Rochester, NY (US)

(72) Inventors: Jared Dwarika, Rochester, NY (US); Sharon Samjitsingh, Rochester, NY (US)

(73) Assignee: HEALTH CARE ORIGINALS, INC., Rochester, NY (US)

( * ) Notice: Subject to any disclaimer, the term of this patent is extended or adjusted under 35 U.S.C. 154(b) by 962 days.

This patent is subject to a terminal disclaimer.

(21) Appl. No.: 17/200,616

(22) Filed: Mar. 12, 2021

(65) Prior Publication Data

US 2021/0199477 A1 Jul. 1, 2021

Related U.S. Application Data (63) Continuation of application No. 15/160,451, filed on May 20, 2016, now Pat. No. 10,955,269.

(51) Int. Cl.
*A61B 5/00* (2006.01)
*G01D 11/30* (2006.01)

(52) U.S. Cl.
CPC ............ *G01D 11/30* (2013.01); *A61B 5/6832* (2013.01); *A61B 5/6833* (2013.01); *A61B 2562/164* (2013.01)

(58) Field of Classification Search
CPC ............. A61B 5/68; A61B 5/6801; A61B 5/6832–6833
See application file for complete search history.

(56) References Cited

U.S. PATENT DOCUMENTS 7,868,914 B2    1/2011  Dengler et al.
2004/0186390 A1 9/2004  Ross et al.
(Continued)

FOREIGN PATENT DOCUMENTS

CN    102015037 A    4/2011
CN    102293992 A    12/2011
(Continued)

OTHER PUBLICATIONS

International Search Report & Written Opinion dated May 26, 2023 from PCT Application No. PCT/2023/061700.
(Continued)

*Primary Examiner* — Joseph A Stoklosa
*Assistant Examiner* — Brian M Antiskay
(74) *Attorney, Agent, or Firm* — INNOVATION CAPITAL LAW GROUP, LLP; Vic Lin (57) ABSTRACT

A wearable and/or a wearable mount solves many issues presented with conventional wearables and wearable mounts. For example, the wearable mount can be designed with a low ratio of adhesive contact area to wearable mount contact area while providing the capability to collect data and/or dispense medication on one specific spot and, further still, allowing the use of an easy to remove adhesive. This configuration may facilitate free movement of the body even when the wearable mount is attached to the skin. The wearable may have surface contacts, removing the need for ports that could be damaged. The adhesive layer can provide insulation and isolating properties for the contacts while the device is being worn. Finally, the wearable may be a patch-type wearable that allows the appearance of the wearable to be changed without the need for housing changes or other costly solutions.

14 Claims, 9 Drawing Sheets

(56) References Cited

U.S. PATENT DOCUMENTS

| | | |
|---|---|---|
| 2006/0136173 A1 | 6/2006 | Case et al. |
| 2006/0229507 A1* | 10/2006 | Kermani ............... A61B 5/6833 |
| | | 600/344 |
| 2007/0100213 A1 | 5/2007 | Dossas et al. |
| 2008/0288026 A1* | 11/2008 | Cross ................. H01R 13/5224 |
| | | 607/60 |
| 2009/0216127 A1 | 8/2009 | Gavriely |
| 2010/0037489 A1 | 2/2010 | Berner, Jr. et al. |
| 2010/0228113 A1* | 9/2010 | Solosko ................ A61N 1/048 |
| | | 600/382 |
| 2011/0035158 A1 | 2/2011 | Banos et al. |
| 2011/0125044 A1 | 5/2011 | Rhee et al. |
| 2011/0144470 A1* | 6/2011 | Mazar .................... A61B 5/257 |
| | | 600/391 |
| 2013/0173461 A1 | 7/2013 | Levy |
| 2014/0221855 A1 | 8/2014 | McCaffrey |
| 2015/0088007 A1 | 3/2015 | Bardy et al. |
| 2015/0094558 A1* | 4/2015 | Russell ................. A61B 5/282 |
| | | 600/386 |
| 2015/0148618 A1 | 5/2015 | Sitko et al. |
| 2015/0351690 A1 | 12/2015 | Toth et al. |
| 2016/0066837 A1 | 3/2016 | Melo |
| 2016/0100808 A1 | 4/2016 | Anbarani |
| 2016/0235323 A1 | 8/2016 | Tadi et al. |
| 2017/0071506 A1 | 3/2017 | Dwarika |
| 2017/0072283 A1 | 3/2017 | Davisson et al. |
| 2019/0290150 A1 | 9/2019 | Felix et al. |

FOREIGN PATENT DOCUMENTS

| | | |
|---|---|---|
| CN | 202859097 U | 4/2013 |
| CN | 205359455 U | 7/2016 |
| CN | 106164817 A | 11/2016 |
| WO | 2006065679 A2 | 6/2006 |
| WO | 2009096630 A1 | 8/2009 |
| WO | 2015044851 A2 | 4/2015 |
| WO | 2015048502 A1 | 4/2015 |

OTHER PUBLICATIONS

International Preliminary Report on Patentability (Chapter II) dated May 17, 2024 from PCT Application No. PCT/2023/061700 (24 pages).

* cited by examiner

WEARABLE APPARATUS

CROSS-REFERENCE TO RELATED APPLICATIONS

This application is a continuation of U.S. patent application Ser. No. 15/160,451, filed May 20, 2016, the contents of which are herein incorporated by reference.

BACKGROUND OF THE INVENTION

1. Field of the Invention

Embodiments of the invention relates generally to wearable apparatus. More particularly, the invention relates to physical design features and specifications for a wearable intended for use on a human body and other applicable mammalian bodies. The wearable may or may not be equipped with sensors to collect information from the body either as contact or close proximity non-contact with or without position specific, zero or minimal drift constraints.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Wearables that are attached to the body by means of adhesives are positioned so to reduce the wearable impinging on the body during use. This is necessary to prevent discomfort for the user. User discomfort leads to reluctance in using the wearable as intended or even discontinued or sporadic use. The wearable must, therefore, accommodate the movement of the body and, due to this fact, wearables are implemented to be worn on portions of the body where surface changes are minimal, e.g., wrist, ear, leg and, where implementation must be elsewhere, the method of attaching the wearable to the body is difficult. The problem with these methods of attaching is that they also contribute to the creation of discomfort for the user via the use of belts, bands, articles of clothing, strong adhesives, large adhesives, and the like.

Conventional wearables often concentrate on large adhesives, covering the entire wearable and a significant amount of area around it with adhesive. Moreover, many conventional wearables use strong adhesives.

Wearables that are intended to collect and or monitor the wearer for a period of time are subject to exposure to moisture, which could lead to a risk that the wearer will short electrical contacts where present on the wearable. To address these issues, conventional wearables include covers to encase electrical ports when the wearable is being worn. Covering the electrical contacts, whether on the surface, protruding or recessed, to guard against contact with the skin is simple enough, however, covering these contacts to prevent or reduce moisture ingress results in the need for tighter sealing or other positive sealing methods. Invariably, these types of covers are rendered inoperative due to daily use either because they are torn off, deformed or damaged, resulting in the same risks identified above. Further still, attempts to make wearables even more robust results in larger form, demanding that the wearable increase in some dimension or dimensions to accommodate it. By nature of being a wearable, the intent is for the device to have a form as small and lightweight as possible to reduce strain on the skin, for functionality, aesthetics, and the like.

When a wearable has a port, the port is typically a micro Universal Serial Bus (USB) port recessed with flip covers, press covers, screw covers, and the like. Some conventional wearables further include a communication port which is present, but seldom used, for field upgrades.

Conventional wearables are at risk of being discarded or used sporadically resulting in reduced efficacy of its intended use. This is of particular interest when the intended use is within the treatment of a chronic disease or other application requiring consistent collection of data or monitoring. Therefore, ways in which users become engaged by the wearable apart from the designed use is an important part of wearable design and operation. Various strategies are employed, e.g., reducing the need for the user to remove the wearable; gamification of accompanying interaction apps and software that relies on consistent use; incorporating into jewelry and other items of clothing; incorporating into other accepted wearable systems like watches or earpieces and, maybe most important of all, allowing the user to change the appearance of the wearable as desired. Depending on the particular application, location of use, terms of use, and the like, the applicability of these approaches differs. Often, a wearable must be worn on the upper torso, be worn for the majority of a day, every day, be used by children and young adults, and the like. Additionally, the wearable should be manufactured at a relatively low cost and cost of use should be minimal. With these competing requirements, most of the above methods cannot be applied and the ability to change the appearance of the wearable is generally an upsell costing a lot more.

There are very few options for users to change the appearance of the wearable. Some conventional wearables that are limb worn, for example, have housings or bands that may be changed.

As can be seen, there are needs for wearables to make them attach to the body to accommodate movement while reducing the ability to cause discomfort for the wearer, to insulate and isolate the contacts whenever the device is in use without the use of sealing mechanisms, and to allow the appearance of the wearable to be changed to reflect the mood of the wearable.

SUMMARY OF THE INVENTION

Embodiments of the present invention provide a system for attaching a wearable to a user, comprising a wearable mount having a skin contacting side and a wearable contacting side; a plurality of spots of first adhesive disposed on a respective plurality of extremities of a portion of the skin contacting side for adhering the wearable mount to the skin, the portion being 50 percent or less of the area of the skin contacting side of the wearable mount; and a second adhesive on a portion of the wearable contacting side of the wearable mount, the second adhesive attaching a portion of the wearable to the wearable mount, the second adhesive providing an insulative layer to insulate contacts of the wearable from direct contact with skin of the user.

Embodiments of the present invention further provide a wearable mount for attaching a wearable to a user comprising a skin contacting side and a wearable contacting side; a first adhesive on a portion of the skin contacting side for adhering the wearable mount to the skin, the portion being 50 percent or less of the area of the skin contacting side of the wearable mount; and a second adhesive on a portion of the wearable contacting side of the wearable mount, the second adhesive configured for attaching a portion of the wearable to the wearable mount, the second adhesive providing an insulation layer between the skin of the user and contacts of the wearable when the wearable is attached to the wearable mount.

Embodiments of the present invention also provide a method to reduce skin irritation when wearing a wearable sensor comprising attaching a plurality of spots of first adhesive disposed on a wearable mount to skin of a user, the wearable mount having a skin contacting side and a wearable contacting side, the plurality of spots of first adhesive disposed on a respective plurality of extremities of a portion of the skin contacting side, the portion being 50 percent or less of the area of the skin contacting side of the wearable mount; and attaching a wearable on a second adhesive disposed on a portion of the wearable contacting side of the wearable mount, the second adhesive providing an insulative layer to insulate contacts of the wearable from direct contact with skin of the user.

In some embodiments, a sensor area of the wearable that needs contact with the skin or placement on a specific spot, provided that such a sensor is needed, has a flat circular area around it. Further still, ideally the wearable should be flexible to allow contouring with the body as it moves. A corresponding wearable mount (also referred to as adhesive layer) has a ring of adhesive corresponding to the designated flat portion of the wearable. This adhesive can be a high strength adhesive and bonds the adhesive layer to the wearable, i.e., does not contact the skin. The area in the center of the designated area of the adhesive layer can be a hole allowing sensors or other such device to contact the skin. The rest of the adhesive layer on the side of the wearable does not stick to the wearable. The skin side of the adhesive layer then has a spot of easy to remove adhesive at each point. For example, a triangular shape would have three spots, a four sided layer may have 4 spots, and the like. Additionally, the adhesive layer can be made from material with sufficient stretch to suit the movement of the body but contains memory allowing it to shrink. For example, if the adhesive layer is attached to the chest area, as someone bends forward using abdominal muscles, the points of the adhesive layer will get closer as the skin contracts, then bending outward may cause the chest area to expand, expanding the adhesive layer with it. Throughout this motion, the skin is not restricted by the reduced elasticity of the wearable, thus reducing the risk of the wearable being uncomfortable. Where the wearable is flexible, the changes in body contour is further accommodated. If a flexible wearable or fixed wearable is attached to the body, as the body moves, the skin stuck to the wearable is forced to shift or pull with the movement. This results in the wearable getting undone. Here, the current market solutions are to employ very strong adhesives or large adhesives covering a wearable. With this embodiment of the present invention, as the adhesive layer can stretch with the skin, easy to peel off adhesives can be used, which is important for long term use of wearables, thus reducing skin damage. With the present invention, as the skin moves around, the wearable "floats" on the wearable mount, reducing the discomfort.

In some embodiments, either incorporated on the wearable or attached as a layer, there is a layer of material that has a higher elasticity than the wearable and, to the extent of possible, skin movement. The wearable side of the adhesive layer can now connect with the wearable on many more points. This provides benefits such as accommodating many sensors, heavier wearables, wearable use under rigorous settings, and the like. So in this use case, as the skin moves, the highly elastic layer of the wearable moves to suit it thereby allowing the skin to move unrestricted thus reducing the discomfort. Again, both restricted and flexible wearables could be used.

In some embodiments, the wearable has all of the necessary contacts on the skin side surface of the wearable, flush with it. Ordinarily, these contacts could touch the skin or moisture could run across them. By pairing and using the wearable only with a suitable adhesive layer, the adhesive layer covers the ports and insulates the ports from the skin. Additionally, adhesive rings can seal the ports, blocking moisture from penetrating to it and/or moving between contacts. The adhesive can be removed when the wearable is placed for charging, thus exposing the low power contacts. Before attaching for use again, a new adhesive is applied, as is required to reduce skin irritation, and, at the same time, to restore the insulating and isolating properties. The end result is that no additional infrastructure is required to affect these two important safeguards, thereby allowing the wearable to have a small form factor. Additionally, covers for ports of conventional wearables get damaged or lost, rendering the device inoperative. It should be noted that the device could be washed with the adhesive off, as wearables tend to have extensive power management components that could detect these activities and shut off the ports for this activity.

In some embodiments, the material used on the underside of the wearable be the same as the outer side, or at least compatible with the adhesive used on the underside. This feature allows an adhesive layer to be placed on the outside of the device. What this does is that it facilitates the sticking of any compatible material, such as paper, foil, plastic, or the like, that is configured as a different shape, color, pattern, or the like, on the outer side of the wearable, effectively changing the appearance of the wearable. This step is not possible today as most wearables have adhesives holding the actual wearable in place which cross the top or the top material is made from materials that are silicone based, reducing its ability to retain adhesives on it. Such a feature allows children to stick on paper, or the like, in different shapes, or with characters, or depicting objects, or the like, thereby giving them comfort as they use the device. It is akin to a child wearing an under vest with their favorite character printed on it as it gives them comfort, especially as they face an uncomfortable situation.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary, a variety of optional components are described to illustrate the wide variety of possible embodiments of the present invention.

As used herein, the term "wearable" or "wearable device" refers to any device that is configured to be worn by a user, typically a mammal user, such as a human. The wearable device may be useful in a variety of applications, such fitness trackers, for remote treatment or monitoring of disorders, as a sports tracker, for health monitoring and data collection, as a gauge for alertness or energy levels, as a navigation tool, as a communication tool, as a medication dispensing device, or the like.

Broadly, embodiments of the present invention relate to a wearable and/or a wearable mount that solves many issues presented with conventional wearables and wearable mounts. For example, the wearable mount can be designed with a low ratio of adhesive contact area to wearable mount contact area while providing the capability to collect data and/or dispense medication on one specific spot and, further still, allowing the use of an easy to remove adhesive. This configuration may facilitate free movement of the body even when the wearable mount is attached to the skin. The wearable may have surface contacts, removing the need for ports that could be damaged. The surface contacts can provide insulation and isolating properties for the contacts while the device is being worn. Finally, the wearable may be a patch-type wearable that allows the appearance of the wearable to be changed without the need for housing changes or other costly solutions.

Figure 1:
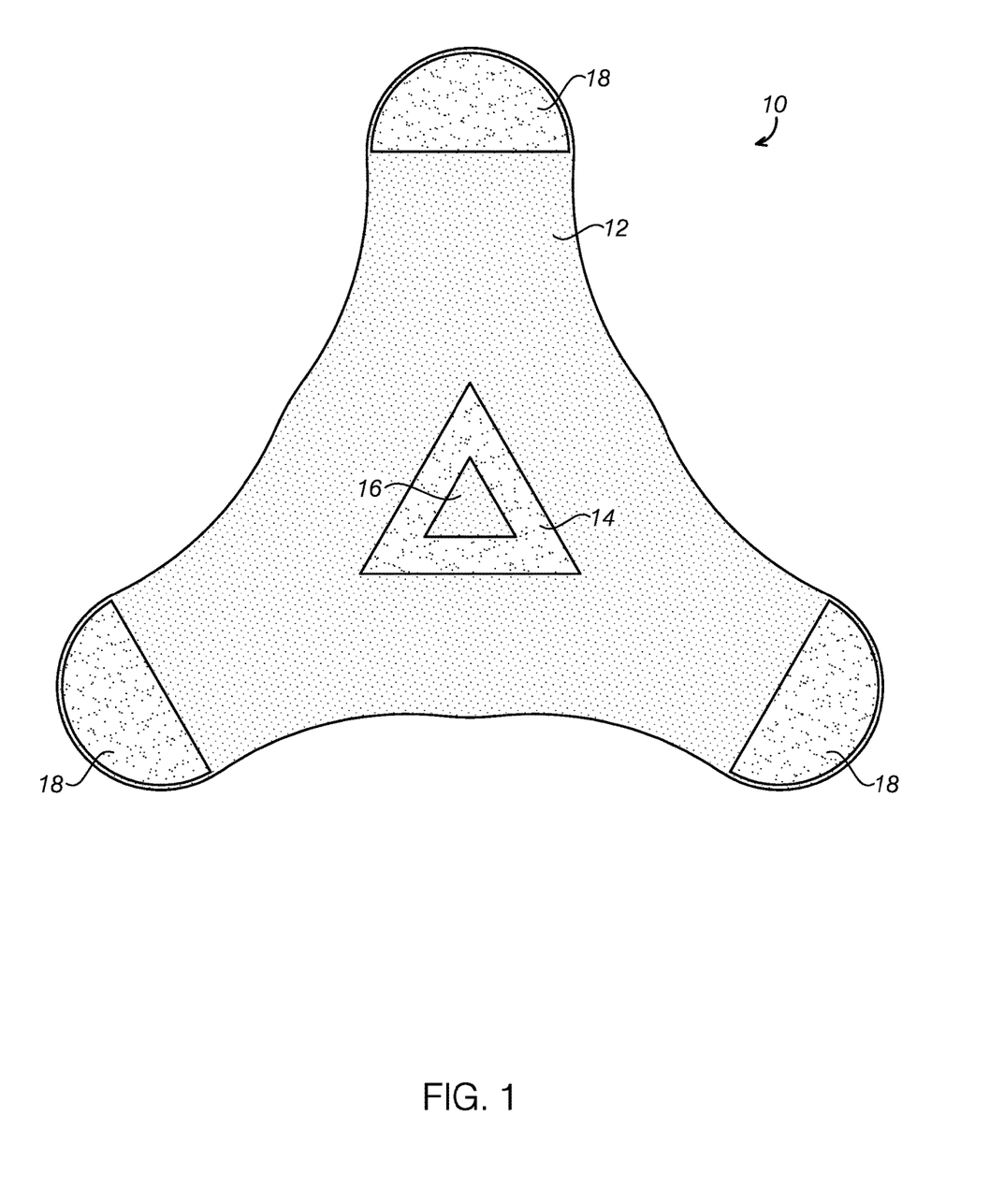
FIG. 1 is a bottom, skin-side, view of an adhesive mount for a wearable device according to an exemplary embodiment of the present invention.

Referring to FIG. 1, a top view of a skin-contacting side 12 of an adhesive layer 10, also referred to as a wearable mount 10, is shown. The adhesive layer 10 can include a center adhesive 14 forming a closed ring and having a cutout 16 within the center adhesive 14, indicating sensor location, for example. The cutout 16 may be dependent on the sensor requirements and may or may not be present. The adhesive 14 may be formed in various shapes. A triangular shaped adhesive 14 is shown in FIG. 1.

Additional adhesive 18 may be disposed on the extremities of the adhesive layer 10. For example, if the adhesive layer 10 is triangular, as shown, then the adhesive 18 may be disposed at each of the three corners of the triangular adhesive layer 10. Similarly, if the adhesive layer 10 is rectangular or square, then the adhesive 18 may be disposed on each of the four corners of the adhesive layer 10. While the Figures show the adhesive 18 at extremities of the adhesive layer 10, other patterns of adhesive 18 to connect the adhesive layer 10 to the user's skin are contemplated within the scope of the present invention. Regardless of design, typically, a low ratio of area of adhesive 18 to area of the bottom side 12 of the adhesive layer 10 is sufficient for attaching the adhesive layer 10 to the user's skin while permitting flexibility during movement of the user. This low ratio may, for example, result in the area of the adhesive 18 being less than 50% of the total area of the bottom side 12 of the adhesive layer 10. Often, the area of the adhesive 18 may be less than 25% of the total area of the bottom side 12 of the adhesive layer, typically, even less than 20% thereof.

Typically, wearables include adhesives that cover the entire skin side, giving rise to many of the issues discussed above. The adhesive placement of the present invention can allow for a fixed region on the skin (when needed) via adhesive 14, as well as allow flexibility by having adhesive 18 only at the extremities of the adhesive layer 10.

The adhesive layer 10 may be formed from an elastic material. In some embodiments, the elastic material may have sufficient elasticity so that user movement is accommodated by the flexibility of the material, where the adhesive 18 remains attached to the skin during movement of the user. In this embodiment, the elastic material of the adhesive layer may be defined as a "high elasticity" adhesive layer.

Figure 2:
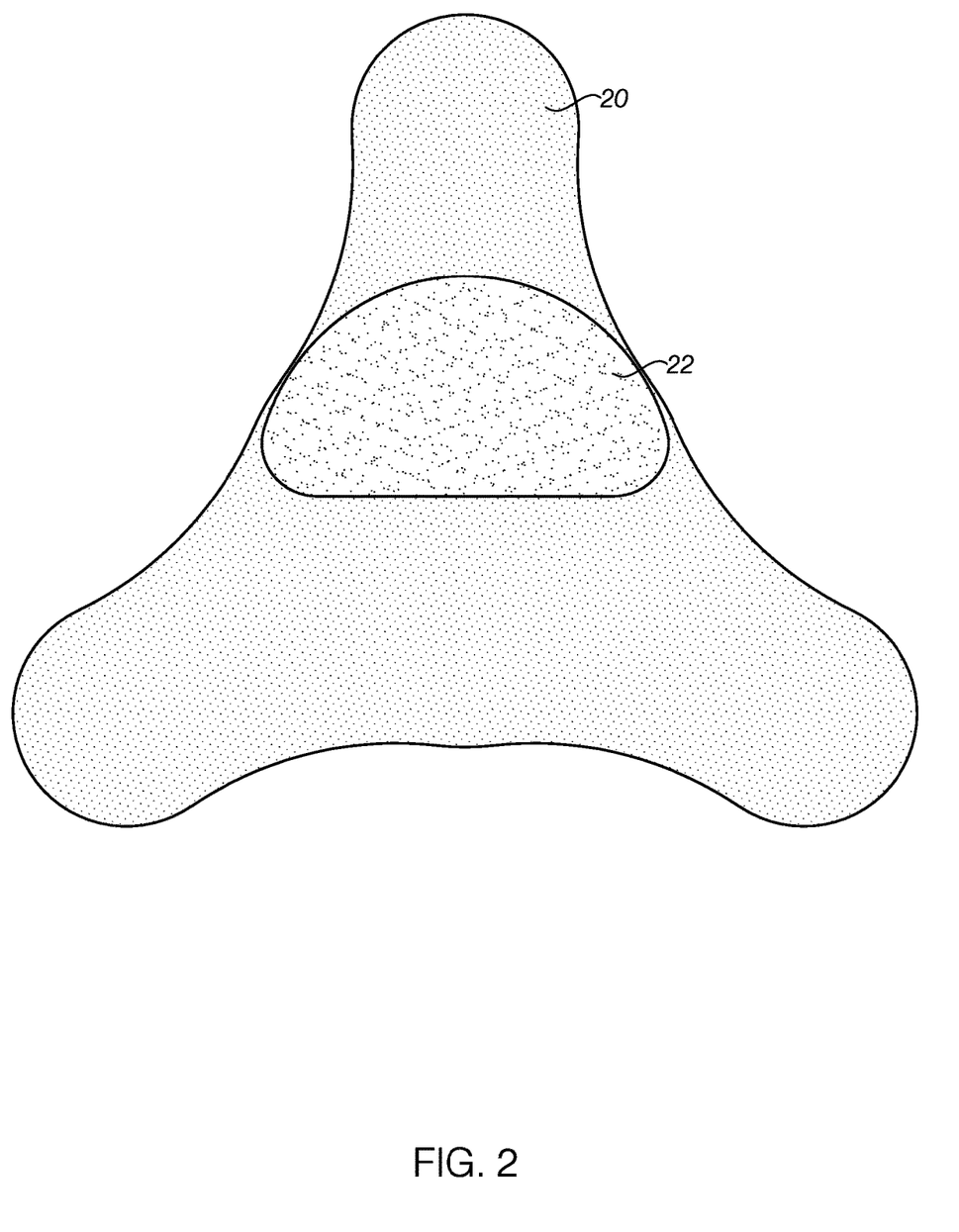
FIG. 2 is a top, wearable device side, view of the adhesive mount of FIG. 1, illustrating an exemplary device side adhesive arrangement.

Referring now to FIG. 2, a wearable mounting side 20 of the adhesive layer 10 is shown. The wearable mounting side 20 can include a device side adhesive 22. The device side adhesive 22 can be disposed generally in the vicinity of the sensors (not shown) of a wearable 40 (see FIG. 5) to keep the wearable firmly bonded to the adhesive layer 10. Moreover, the shape of the adhesive 22 can be designed to cover the contacts 46 of the wearable 40 (see FIG. 5), as discussed in greater detail below.

Figure 3:
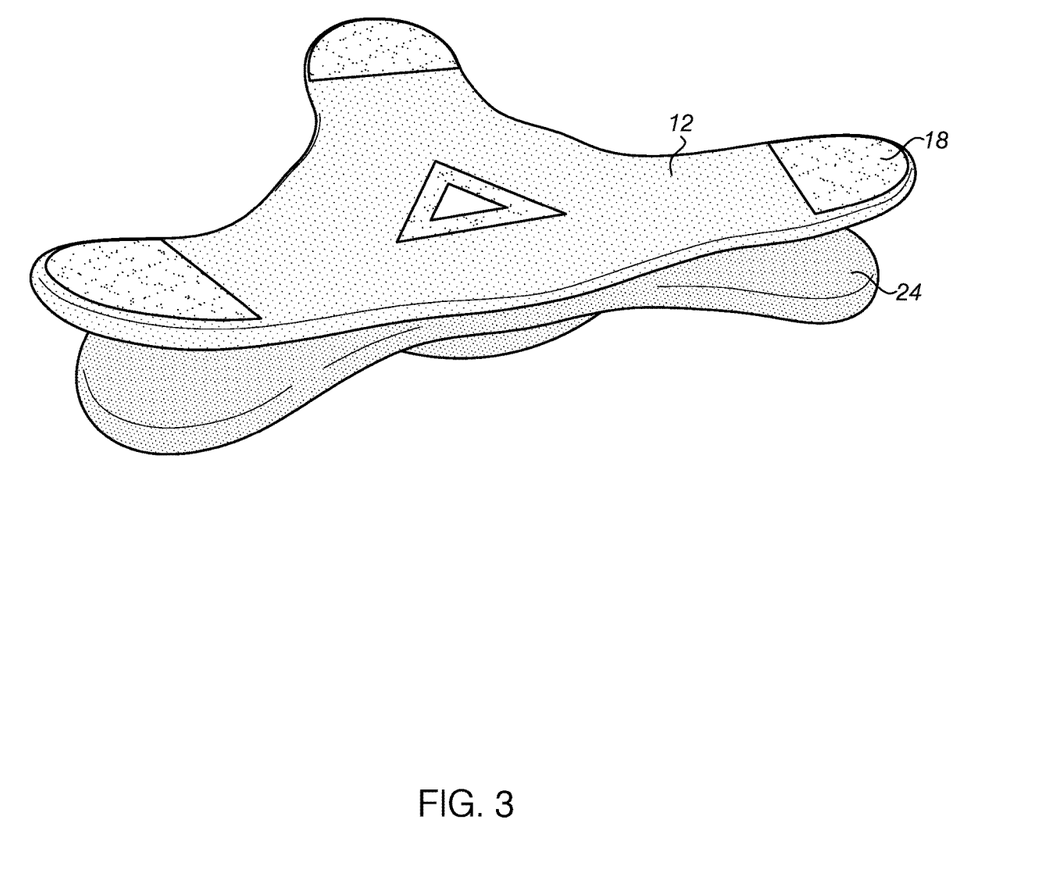
FIG. 3 is a bottom, skin-side perspective view of a wearable device attached to an adhesive mount.

Referring to FIG. 3, a mounted wearable 24 can be attached to the adhesive mount 10, where the adhesive 18 is used to attach the adhesive mount 10 to a user's skin. As can be seen, in some embodiments, the wearable 24 is attached to the adhesive mount 10 at a portion thereof thereby permitting flex of the adhesive mount 10 when the user moves. In this embodiment, the mounted wearable 24 may be stiff or flexible. In some embodiments, the mounted wearable 24 is flexible and can be attached to the adhesive mount 10 with a greater surface area of adhesive.

It should be noted that the adhesives 14, 18, 22 and the adhesive layer 10 can be designed in various thicknesses, colors, shapes and designs. Such embodiments, while not specifically illustrated or described, are included within the scope of the present invention.

Figure 4:
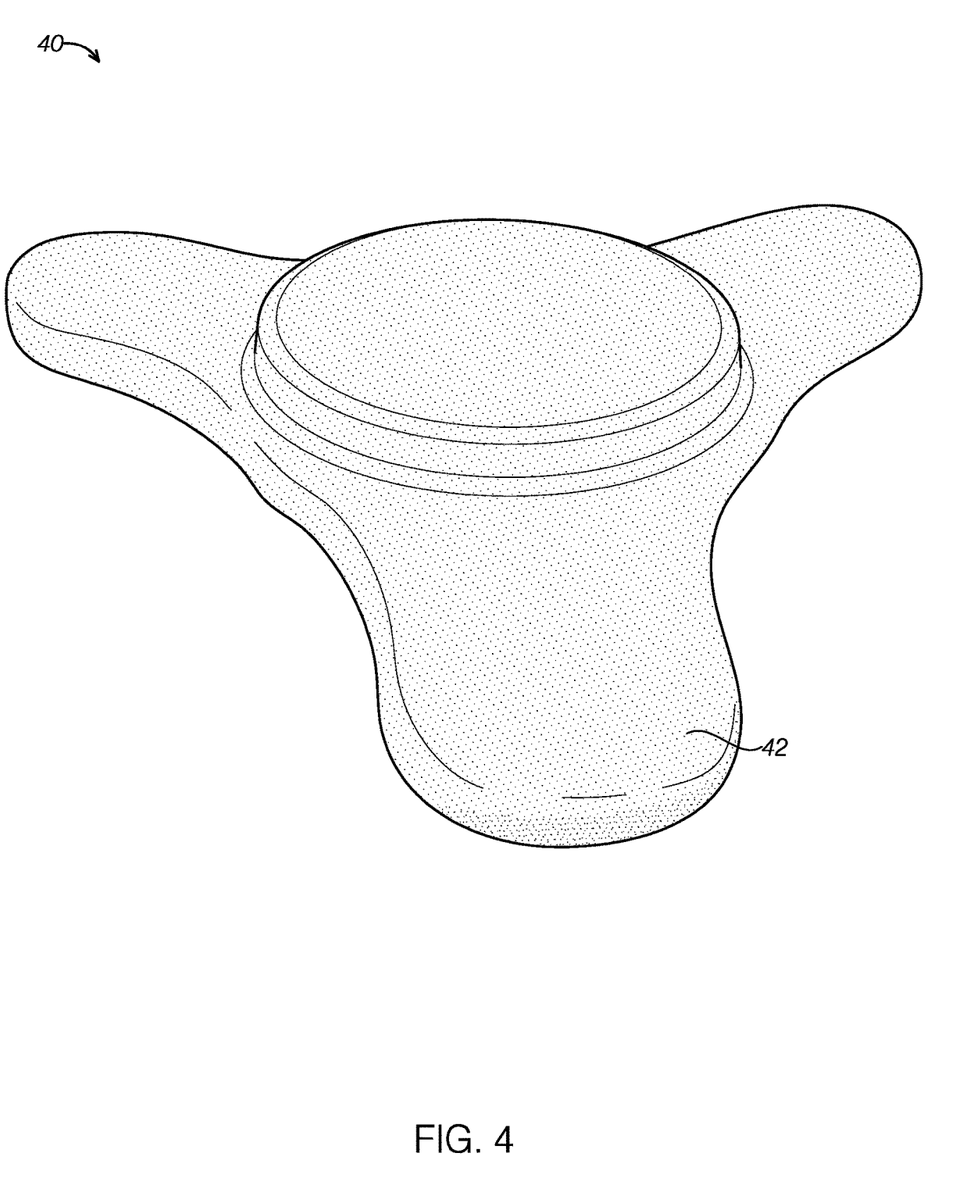
FIG. 4 is top perspective view of a wearable device usable with the adhesive mount of FIG. 1.
Figure 5:
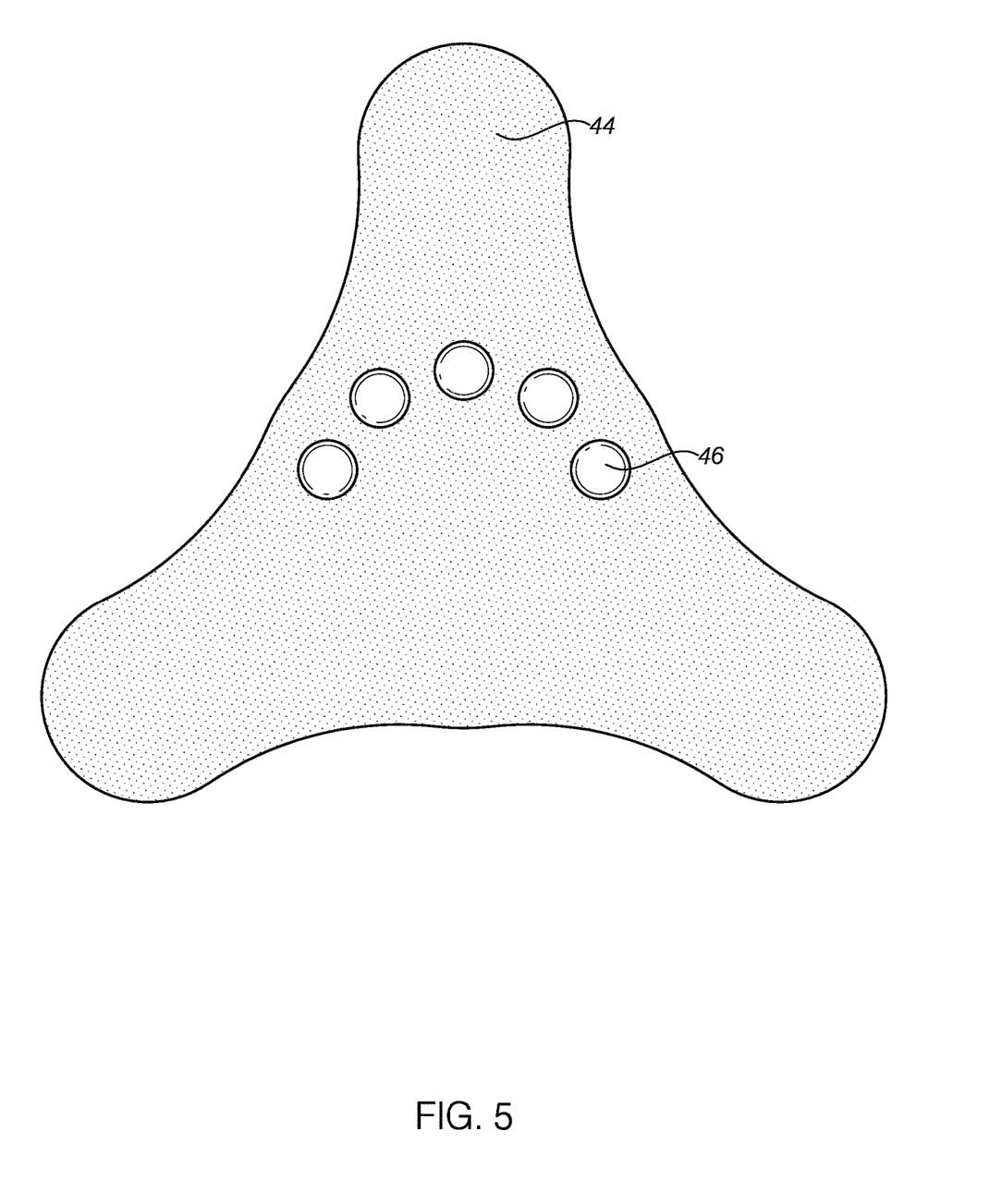
FIG. 5 is a bottom view of the wearable device of FIG. 4, illustrating exemplary flush contacts according to an embodiment of the present invention.
Figure 6:
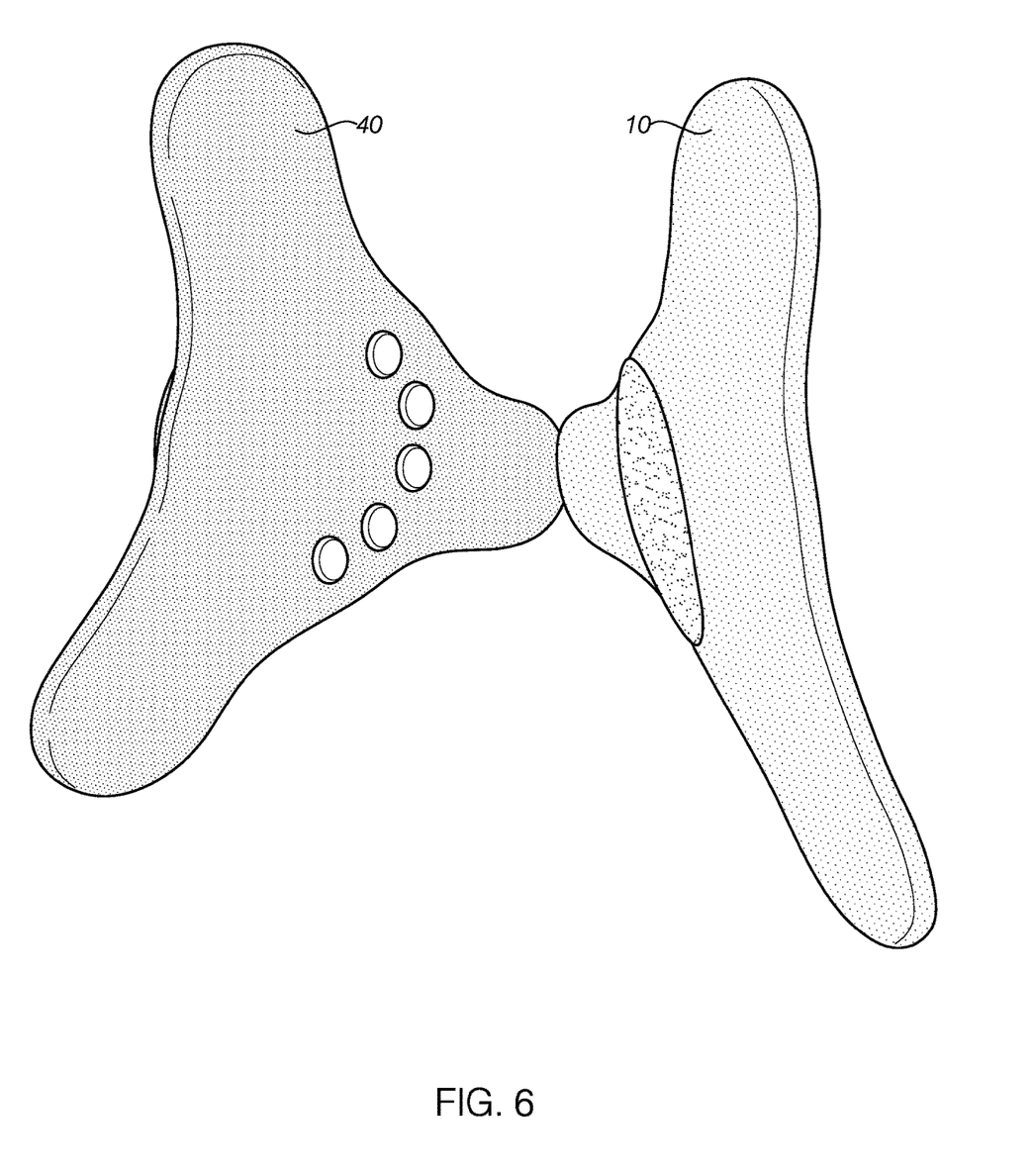
FIG. 6 is a side perspective view illustrating a wearable device being aligned with the adhesive mount of FIG. 1.

FIG. 4, a top side 42 of the wearable 40 is shown. FIG. 5 shows a bottom side 44, also referred to as adhesive layer contacting side, of the wearable 40. FIG. 6 shows the bottom side 44 of the wearable 40 being mounted to the adhesive layer 10. As discussed above, typical wearables can include ports for charging, updates, data transfer, or the like. These ports can be damaged by moisture.

Figure 7:
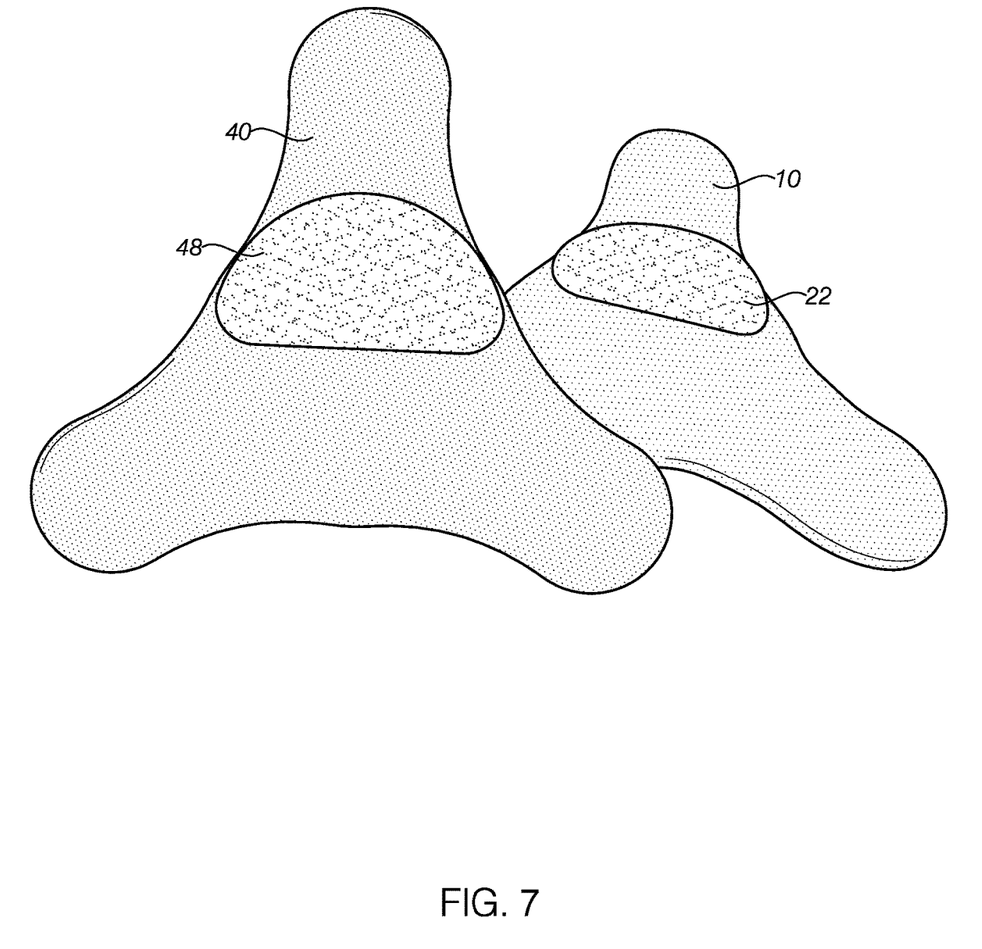
FIG. 7 is a front perspective view illustrating the wearable device and adhesive mount of FIG. 6, with adhesive covering, insulating and isolating the contacts of the wearable device according to an embodiment of the present invention.

The wearable 40, according to embodiments of the present invention, can include flush contacts 46 positioned in a location where the wearable 40 is attached to the adhesive layer 10. While a particular number and pattern of contacts 46 are shown in FIGS. 5 and 6, various numbers and patterns of contacts 46 may be used, as needed by a particular application, within the spirit of the present invention. Therefore, when the adhesive 22 (see FIG. 2) is attached to the wearable 40, the adhesive 22 covers the contacts 46. In some embodiments, as shown in FIG. 7, adhesive 48 may be applied over the contacts 46 to ensure that the contacts are isolated and insulated. When access to the contacts 46 is needed, one can simply remove the adhesive 48.

Figure 8:
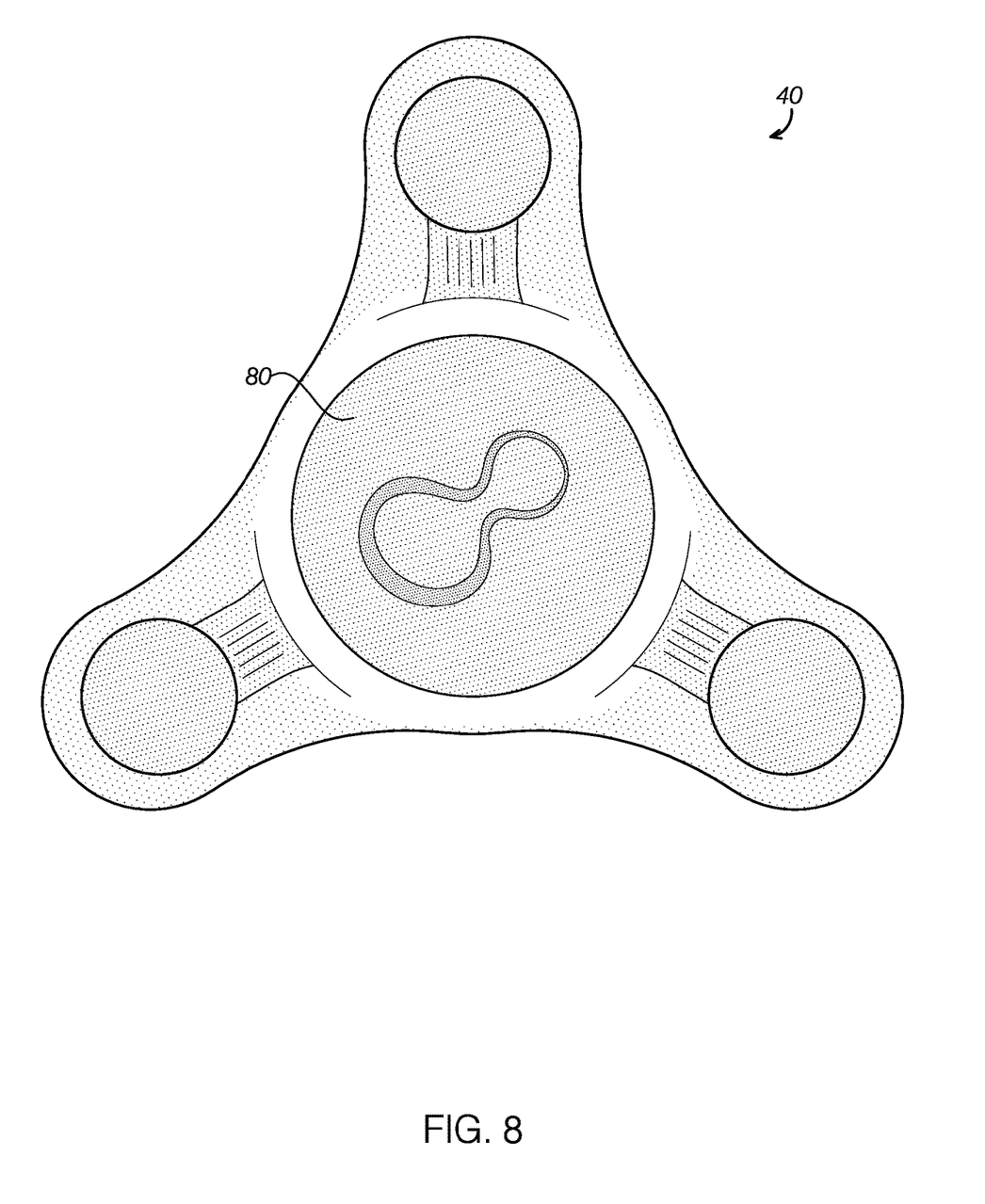
FIG. 8 is a top view of a wearable device with a central region made compatible with wearable adhesive, allowing interchange of designs on the top portion thereof.
Figure 9:
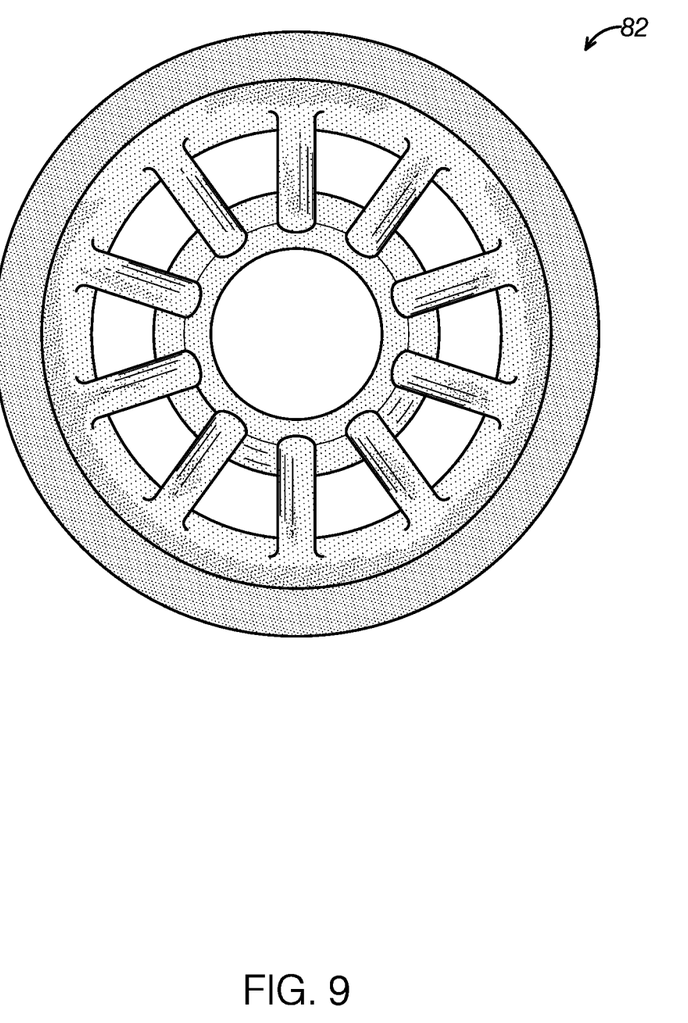
FIG. 9 is a top view of a cutout adapted to be adhered to the top of the wearable device of FIG. 8 with wearable adhesive.

Referring now to FIGS. 8 and 9, in some embodiments of the present invention, the wearable 40 can include at least one adhesive adhering region 80 on a top surface thereof. The adhesive adhering region 80 can be formed from a material conducive to adhering to typical adhesives used for wearables. Typical top surfaces of wearables are made from materials to which wearable adhesives will not adhere, such as silicone. In embodiments of the present invention, all or a portion of the top surface of the wearable 40 can be formed of a material similar to or the same as the bottom surface onto which adhesive 48 is capable of bonding.

With the presence of the adhesive adhering region 80, a user can apply various cutouts 82, such as that shown in FIG. 9, by the use of the same adhesive used to apply the wearable 40 to the adhesive mount 10. Thus, the user can change the color and design of the outer surface of the wearable 40 as desired. If a further change is desired, the user can simply remove the cutout 82 and its adhesive and attach a new design via additional adhesive. The cutout 82 shown in FIG. 9 is an Iron Man power source image and is the property of Marvel Comics. This cutout 82 is shown only as an example, and various sizes, shapes, designs, colors, and the like, of the cutout 82 are contemplated within the scope of the present invention.

The above embodiments of the present invention provide several features to distinguish itself from conventional wearable and wearable mounts. Some of these features, while not inclusive of all such features, are described below.

Embodiments of the present invention allow the use of less adhesives, thereby reducing the risk of skin irritations. In these embodiments, spots of adhesive are placed on the corners and at the main sensor area rather than on the entire profile of the adhesive layer. Embodiments of the present invention further allow the use of easy peel adhesives that reduce the risk of damaging the skin. Conventional wearables often use bandage-type adhesives intended for wound closures. Embodiments of the present invention allow the wearable to move independently of the skin except for the small central anchor point, thereby reducing discomfort arising from movement. Conventional wearables use fixed adhesives solidly bonded to the skin thereby restricting the skin from moving freely. The arrangement of adhesives reduces the amount of adhesives used in each application, reducing the overall cost of the adhesive component, thereby reducing the operating cost of the system.

Embodiments of the present invention allow power and communications to take up as little space as possible, basically just the space of surface contacts. Conventional wearables include bulky ports dictating the thickness of the wearable. Embodiments of the present invention allow electrical contacts to be insulated and isolated with the same adhesive being used each day. Conventional wearables have port covers and slides that get torn or lost rendering the device inoperable. The contacts of the present invention are generally a lot less expensive than ports with covers. Moreover, the contacts of the present invention reduce the complexity of the manufacturing process.

Embodiments of the present invention allow the wearable to have its appearance changed by simply sticking new patterns on it via the use of already supplied adhesive. This allows the appearance media to be of simple manufacture, such as a printout or cutout, or the like. This further allows the wearable to take on shapes and characters that are appealing to the user, thereby increasing adherence to using.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A wearable system comprising:
    a wearable, comprising:
        contacts on a skin side surface of the wearable; and
    a wearable mount for attaching the wearable to a user, comprising:
        a skin contacting side and a wearable contacting side;
        a first adhesive on a portion of the skin contacting side for adhering the wearable mount to the skin, the portion being 50 percent or less of the area of the skin contacting side of the wearable mount;
        a second adhesive on a portion of the wearable contacting side of the wearable mount, the second adhesive configured for attaching a portion of the wearable to the wearable mount, the second adhesive directly contacting the wearable to provide an insulation layer to insulate the contacts of the wearable when the wearable is attached to the wearable mount;
        a continuous perimeter of adhesive disposed on an interior of the skin contacting side of the wearable mount, the continuous perimeter of adhesive disposed opposite at least a portion of the second adhesive; and
        a space formed within the continuous perimeter of adhesive, the space is a cutout formed inside the wearable mount.

2. The wearable system of claim 1, wherein the wearable mount is formed from a material having a high elasticity.

3. The wearable system of claim 1, wherein the portion of the wearable contact side having the second adhesive has an area smaller than an area of an attachment side of the wearable.

4. The wearable system of claim 1, wherein:
    at least a portion of a top surface of the wearable is formed from an adhesive adhering material; and
    one or more replaceable portions are configured to be adhered to the portion of the top surface of the wearable.

5. The wearable system of claim 1, wherein the contacts are one or more flush contacts disposed on a surface of the wearable.

6. The system of claim 1, wherein the portion of the wearable contact side having the second adhesive has an area smaller than an area of an attachment side of the wearable.

7. The system of claim 1, wherein at least a portion of a top surface of the wearable is formed from an adhesive adhering material.

8. The system of claim 7, wherein the adhesive adhering material is a material that is the same as a bottom surface of the wearable.

9. The system of claim 7, further comprising one or more replaceable portions configured to be adhered to the portion of the top surface of the wearable.

10. The system of claim 1, wherein the wearable mount is formed from a material having an elasticity to permit stretching of the wearable mount with movement of the user.

11. The system of claim 1, further comprising a wearable adhesive disposed over the contacts of the wearable.

12. A method to reduce skin irritation when wearing a wearable sensor, the method comprising:
    attaching a plurality of spots of first adhesive disposed on a wearable mount to skin of a user, the wearable mount having a skin contacting side and a wearable contacting side, the plurality of spots of first adhesive disposed on a respective plurality of extremities of a portion of the skin contacting side, the portion being 50 percent or less of the area of the skin contacting side of the wearable mount;
    attaching a wearable on a second adhesive disposed on a portion of the wearable contacting side of the wearable mount, the second adhesive providing an insulative layer to insulate contacts on a skin side of the wearable from direct contact with skin of the user;
    attaching a continuous perimeter of adhesive on an interior of the skin contacting side of the wearable mount to the skin of the user at a location for placement of the wearable, wherein a space formed within the continuous perimeter of adhesive, the space is a cutout formed inside the wearable mount.

13. The method of claim 12, further comprising disposing a wearable adhesive over the contacts of the wearable.

14. The method of claim 12, wherein the portion of the wearable contact side having the second adhesive has an area smaller than an area of an attachment side of the wearable.

* * * * *